May 16, 1967 H. W. STEINDORF Plant Pat. 2,742
APRICOT OR PRUNUS ARMENIACA
Filed Oct. 14, 1965
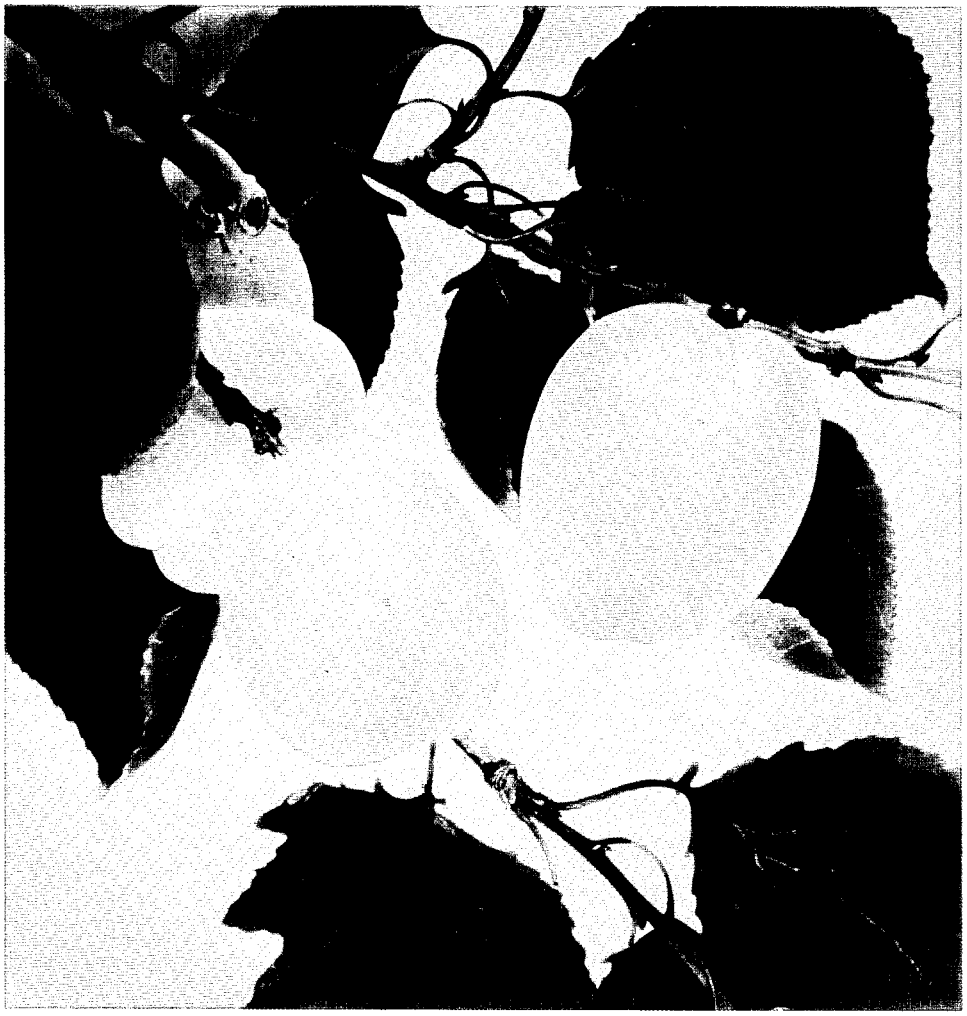
INVENTOR:
HERBERT W. STEINDORF
BY Hansen and Lane
ATTORNEYS

United States Patent Office

Plant Pat. 2,742
Patented May 16, 1967

2,742
**APRICOT OR *PRUNUS ARMENIACA***

Herbert W. Steindorf, Rte. 2, Box 280, Gilroy, Calif. 95020

Filed Oct. 14, 1965, Ser. No. 496,194
1 Claim. (Cl. Plt.—39)

My new discovery relates to a new and distinct variety of apricot or *Prunus armeniaca,* originating as a sport of the parent variety, Blenheim apricot, and is characterized by its habit of blooming and bearing approximately thirty days later than the parent Blenheim apricot.

A substantial portion of the canning apricots grown in the United States are used in the packing or canning of a product known in the canning industry as "Fruit Salad." This product employs apricots and other fruits, including peaches, pears, pineapple, and grapes, and a few maraschino cherries for color.

The Blenheim apricot, the parent of the present new variety, is the variety used almost exclusively in the United States of America in canning. These Blenheim apricots ripen approximately thirty days before the other fruits, except cherries, used in the making of fruit salad, so that it is the present practice to pre-can the apricots and other required fruits in one gallon cans, and then to make the fruit salad from these pre-canned fruits at the end of the canning season.

This procedure, of course, adds greatly to the cost of producing fruit salad over what it would be if it could be produced from fresh fruit without the necessity of pre-canning. For example, the product known as "Fruit Cocktail," which uses substantially the same fruits as fruit salad, but without the apricots, is produced directly from the fresh fruits, with the exception of the cherries, which are pre-canned, and its cost is approximately one-third that of fruit salad.

My present variety of apricot originated as a sport branch on one of the Blenheim apricot trees in an apricot orchard owned by me in Santa Clara Valley, Calif. It was first noted that the apricots on this branch were still hard and green when the other fruit on the remainder of the tree and in the rest of the orchard, was harvested. Later it was noted that the fruit on this sport branch did not ripen until a month after the remainder of the crop had been harvested.

One specific bud, from about the middle of this sport branch, produced excellent fruit, which ripened approximately thirty days later than the regular Blenheim crop and which appears to be no more subject to cracking than standard Blenheim fruit.

The growth produced from this one specific bud has now been reproduced by successive budding and grafting onto other apricot trees and root stock of varieties used commonly for producing Blenheim apricots, with the uniform result that the fruit from this budded and grafted stock ripens approximately thirty days later than the regular or parent Blenheim apricot crop.

Some of the fruit from a tree produced by the foregoing budding and grafting procedure was tested by a large canning company in 1958, and was found to be similar in all respects to a regular Blenheim apricot, with the exception that it may have a somewhat higher sugar content. If this proves to be the case, it may be due to the fact that the fruit of my new variety develops later in the season than the fruit on the parent variety, when the heat and sunshine are more intense. The trees produced by budding and grafting from this one original bud on the sport branch seem somewhat more vigorous than the regular or parent Blenheim apricot. The flowers and fruit of the resultant trees are in all other respects similar to those of the regular, or parent Blenheim apricot.

The late blooming habit of my new variety has an additional advantage in that the crop would not ordinarily be damaged by an unseasonal late frost.

The accompanying illustration shows the approximate shape and coloration of the branches, leaves and fruit of my new variety, which I designate the Steindorf apricot.

*Name.*—Steindorf.

*Parentage.*—Sport of Blenheim apricot.

It has been reproduced asexually by budding and grafting since 1948.

*Flowers.*—Flowers are in all known respects similar to those of the parent Blenheim apricot, but bloom approximately thirty days later than the parent trees.

*Tree.*—The tree is similar in all known respects to the parent Blenheim apricot, but is apparently somewhat more vigorous.

*Foliage.*—The foliage is generally similar to the foliage of the parent Blenheim apricot.

*Branching.*—The branching arrangement and strength are similar to those of the parent Blenheim apricot.

*Pruning pattern.*—Recommended pruning pattern is the same as for the parent Blenheim apricot.

*Fruit.*—The fruit of my new variety is, as nearly as can be determined, of the same conformation, texture and coloration as the skin and the flesh of the parent Blenheim apricot, but may be somewhat larger and sweeter, the latter two factors being unproven to date, but if present may be due, as mentioned previously herein, to the warmer and sunnier later fruiting season.

*Pit.*—The pit of the fruit of my new variety is of the same structure, size and color as that of the parent Blenheim apricot.

*Maturity.*—As mentioned previously herein, the late flowering and ripening of the fruit are the dominant differences between my present new variety and the parent Blenheim apricot. The trees flower and the fruit ripens approximately thirty (30) days later than the parent Blenheim apricot.

Having thus disclosed my invention, I claim:

A new and distinct variety of Blenheim apricot, substantially as herein shown and described, characterized particularly by the flowering and maturing of the fruit being approximately thirty (30) days later than the flowering and maturing of the fruit of the parent Blenheim apricot.

No references cited.

ABRAHAM G. STONE, *Primary Examiner.*

ROBERT E. BAGWILL, *Examiner.*